(12) United States Patent
Andrieu et al.

(10) Patent No.: US 8,486,154 B2
(45) Date of Patent: Jul. 16, 2013

(54) RESORBABLE INTRA-URETHRAL PROSTHESIS

(75) Inventors: Raymond Andrieu, Yens (CH);
Philippe Le Goff, Epalinges (CH);
Milan Krajicek, Prague (CZ); Vaclav Vomacka, Prague (CZ)

(73) Assignee: Cerebel - Invest SA, Lausanne (CH)

( * ) Notice: Subject to any disclaimer, the term of this patent is extended or adjusted under 35 U.S.C. 154(b) by 808 days.

(21) Appl. No.: 12/513,405

(22) PCT Filed: Nov. 6, 2006

(86) PCT No.: PCT/IB2006/003117
§ 371 (c)(1),
(2), (4) Date: Dec. 28, 2009

(87) PCT Pub. No.: WO2008/056194
PCT Pub. Date: May 15, 2008

(65) Prior Publication Data
US 2011/0238019 A1    Sep. 29, 2011

(51) Int. Cl.
*A61F 2/04* (2006.01)
*A61M 5/32* (2006.01)
(52) U.S. Cl.
USPC .................. 623/23.66; 604/265
(58) Field of Classification Search
USPC .................. 623/1.15–23.66; 604/265
See application file for complete search history.

(56) References Cited

U.S. PATENT DOCUMENTS

| | | | |
|---|---|---|---|
| 4,955,859 A * | 9/1990 | Zilber | 604/8 |
| 5,290,271 A | 3/1994 | Jernberg | |
| 5,308,338 A * | 5/1994 | Helfrich | 604/175 |
| 5,549,664 A * | 8/1996 | Hirata et al. | 623/1.48 |
| 5,578,075 A | 11/1996 | Dayton | |
| 5,810,786 A * | 9/1998 | Jackson et al. | 604/265 |
| 6,193,752 B1 * | 2/2001 | Hildebrandt | 623/11.11 |
| 6,245,103 B1 * | 6/2001 | Stinson | 623/1.22 |
| 6,254,632 B1 * | 7/2001 | Wu et al. | 623/1.15 |
| 6,602,281 B1 * | 8/2003 | Klein | 623/1.15 |
| 6,641,607 B1 * | 11/2003 | Hossainy et al. | 623/1.15 |
| 6,652,582 B1 * | 11/2003 | Stinson | 623/1.39 |
| 7,163,555 B2 * | 1/2007 | Dinh | 623/1.42 |
| 7,347,870 B1 | 3/2008 | Andrieu et al. | |
| 8,100,963 B2 * | 1/2012 | Roth et al. | 623/1.42 |
| 2002/0038146 A1 * | 3/2002 | Harry | 623/1.16 |
| 2004/0034405 A1 * | 2/2004 | Dickson | 623/1.11 |
| 2004/0093069 A1 * | 5/2004 | Priewe et al. | 623/1.15 |
| 2005/0177118 A1 * | 8/2005 | Hoganson et al. | 604/288.01 |
| 2006/0217801 A1 * | 9/2006 | Rosenthal | 623/1.46 |

(Continued)

FOREIGN PATENT DOCUMENTS

| DE | 26 54 658 | 6/1977 |
|---|---|---|
| EP | 1284688 | 2/2003 |
| GB | 1 565 828 | 4/1980 |
| WO | 00/74744 | 12/2000 |

OTHER PUBLICATIONS

International Search Report dated Apr. 26, 2007, from corresponding PCT application.

*Primary Examiner* — Suzette J Gherbi
(74) *Attorney, Agent, or Firm* — Young & Thompson

(57) ABSTRACT

The device made in a resorbable material intended to be placed in urethra for Treatment of stricture has the shape of a tube (1), the wall of which has offices (2).

19 Claims, 2 Drawing Sheets

U.S. PATENT DOCUMENTS

| | | | |
|---|---|---|---|
| 2007/0207186 A1* | 9/2007 | Scanlon et al. | 424/424 |
| 2009/0124956 A1* | 5/2009 | Swetlin et al. | 604/8 |
| 2009/0182404 A1* | 7/2009 | Shokoohi | 623/1.11 |
| 2009/0285975 A1* | 11/2009 | Bates et al. | 427/2.25 |
| 2009/0306766 A1* | 12/2009 | McDermott et al. | 623/1.16 |
| 2010/0021519 A1* | 1/2010 | Shenoy | 424/423 |
| 2010/0217227 A1* | 8/2010 | Braun et al. | 604/500 |
| 2011/0270205 A1* | 11/2011 | Odermatt et al. | 604/368 |
| 2012/0035715 A1* | 2/2012 | Robida et al. | 623/1.36 |
| 2012/0150096 A1* | 6/2012 | Li et al. | 604/8 |

* cited by examiner

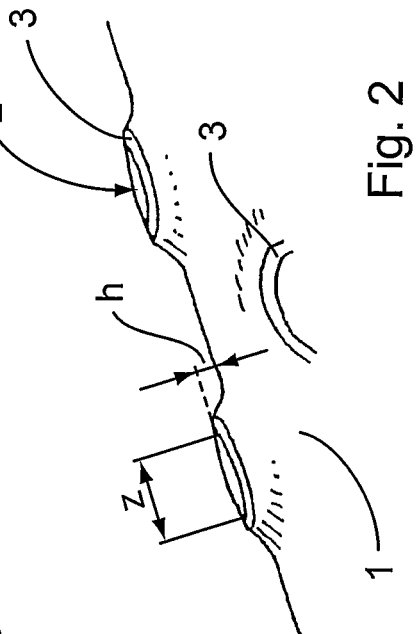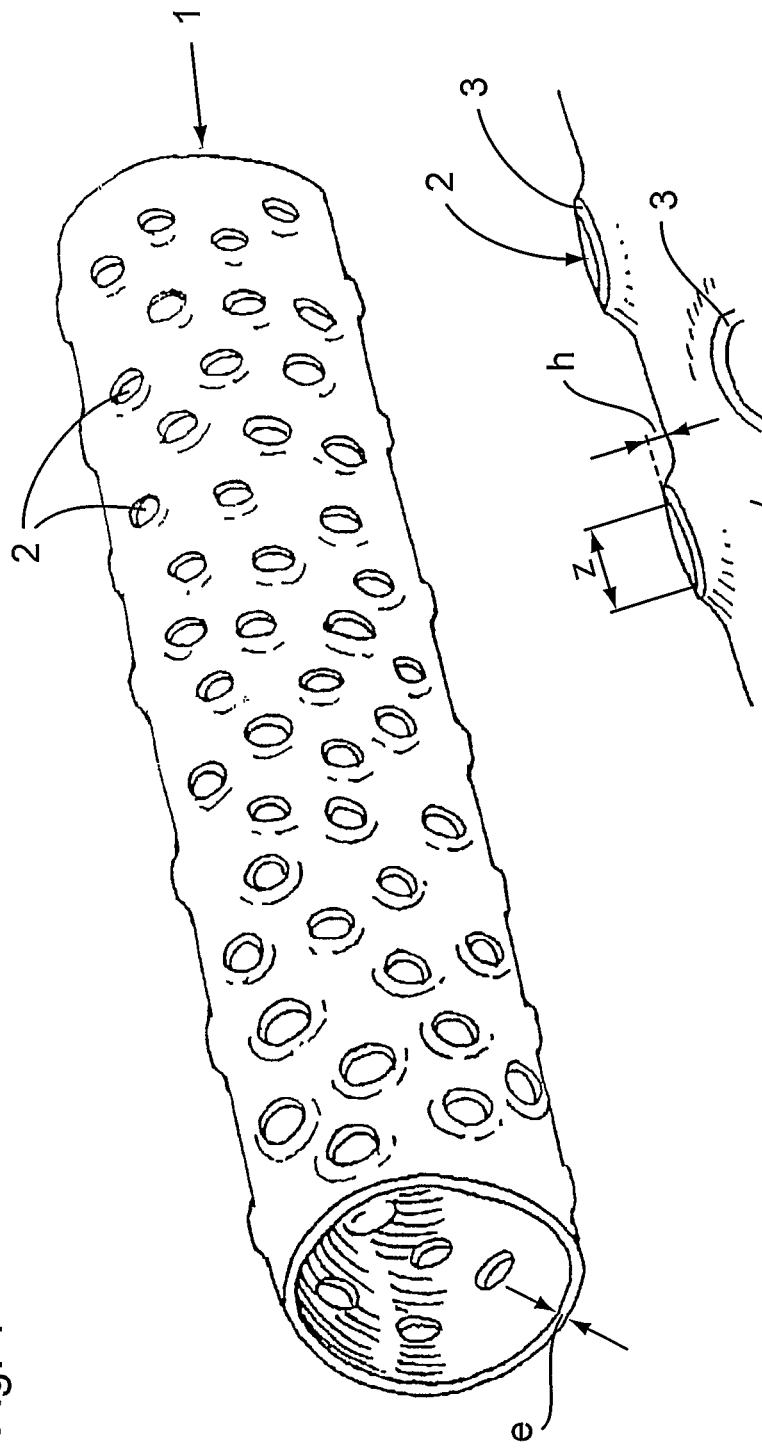
Fig. 1
Fig. 2

RESORBABLE INTRA-URETHRAL PROSTHESIS

FIELD OF THE INVENTION

The device or prosthesis in accordance with the present invention solves the problem of therapy and prevention of repetitive strictures of man's urethra.

BACKGROUND OF THE INVENTION

The stricture of the rear part of the urethra is quite serious urological problem, particularly when all around the world the number of transurethral surgical procedures is significantly rising. In a fair number of cases, after shorter or longer period of time, emerge the problem with urination due to the stricture in the rest of the urethra.

Urethral stricture is when the urethra, the tube that leads from the bladder out of the body, is scarred by an infection or injury and narrows, eventually reducing or blocking the flow of urine from the bladder.

Since males have a substantially longer urethra than females, urethra stricture is common in men, but rare in women. Urethral stricture can vary depending on the cause of scarring and length of the scar.

Urethral stricture may be caused by inflammation or scar tissue from surgery, disease, or injury. It may also be caused by external pressure from an enlarging tumor near the urethra, although this is rare. Increased risk is associated with men who have a history of sexually transmitted disease (STD), repeated episodes of urethritis or benign prostatic hyperplasia (BPH). There is also increased risk of urethral stricture after an injury or trauma to the pelvic region. Any instrument inserted into the urethra (such as a catheter or cystoscope) increases the chance of developing urethral strictures. Urethral stricture may totally block urine flow, causing acute urinary retention, a condition that must be alleviated rapidly.

Satisfactory treatment, i.e. a generally accepted therapeutic approach, is not available. Moreover, urethral stricture is very dreaded and therapeutically difficult situation which can any surgeon hardly avoid. Today main therapeutic approaches are briefly described hereafter.

Placement of a suprapubic catheter, which allows the bladder to drain through the abdomen, may be necessary to alleviate acute problems such as urinary retention. Dilatation of the urethra may be attempted by inserting a thin instrument to stretch the urethra under local anaesthesia. If urethral dilation is not possible, surgery may be necessary to correct the condition. Surgical options vary depending on the location and the length of the stricture.

Cystoscopic visual urethrotomy may be all that is needed for small stricture. A urethral stent for cystoscopic insertion may also be used.

An open urethroplasty may be performed for longer stricture by removing the diseased portion or replacing it with other tissue. The results vary depending on the size and location of urethroplasty, the number of prior therapies, and the experience of the surgeon.

There are no drug treatments or prevention currently available for this disease. About therapeutic misgiving witnesses also a number of plastic procedures with use of dermal lobes, transplants from buccal mucous membranes and so on were used in one or more stages. If all else fails, a urinary diversion—appendicovesicostomy (Mitrofanoff procedure)—may be performed to allow the patient to perform self-catheterization of the bladder through the abdominal wall.

One shall then notice from above description that a unified, generally accepted, therapeutic approach does not exist. Most often the dilatation is used, but it has only a temporary effect and must be again and again repeated. A high percentage of recidivisms have also the longitudinal cutting of the stricture by a cold blade or laser. Also metallic stents, if employed, are not successful due to chronic irritation with followed up hyperplasia. Presently there is no therapeutic approach which offers such results, that it can be considered as the gold standard.

The problem of strictures of rest urethra has very significant medical as well as social impact and improvement in the fate of these patients would be serious contribution to their therapy and quality of life.

It is also important to have an accurate diagnosis and assessment of the location and length of the urethral stricture, and to identify the underlying cause. But without appropriate treatment, the stricture will recur almost 100 percent of the time.

SUMMARY OF THE INVENTION

The invention relates to a resorbable device or prosthesis for use in prevention and/or treatment of urethral stricture.

The device of the invention is intended to first, once inserted, maintain urethral diameter at the desired size and secondly reinforce, while the prosthesis resorbs according to control kinetics, the urethral wall and prevent stricture occurrence by enhancement of fibrotic tissue along the external device surface.

This dual function of the device of the invention is allowed by the adapted shape of the prosthesis and by the used material. Both are necessary for a successful usage of the device.

The shape of the device is intended to independently allow the longitudinal flow of urine and the radial mucous drainage while maintaining the prosthesis at the desired location by a simple sutureless wall adhesion.

The used material is engineered in a biocompatible resorbable synthetic or natural polymer with adapted mechanical and chemical properties to get the desired rigidity, resistance and friction and to concurrently bio-absorbs while promoting fibrotic tissue formation that will act a comparative role once the prosthesis would have fully resorbed.

The device or prosthesis of the invention mainly consists in a tube made in a polydioxanone polymer sized at the desired dimensions (inner and outer diameters, cone angle, and length) with a specific treatment of the external surface creating roughness and a net of small radial orifices with slightly arising margins.

The resorbable intra-urethral prosthesis according to the invention distinguishes itself by the characteristics given in claim 1 and different embodiments are defined according to the dependant claims.

DRAWINGS

The attached drawings show schematically and by way of example two embodiments of the resorbable intro-urethral prosthesis or device according to the invention.

FIG. 1 is a schematic view of a first embodiment of the prosthesis.

FIG. 2 is a detailed view of the surface of the prosthesis.

DESCRIPTION OF THE INVENTION, PREFERRED EMBODIMENTS

Figure 3:
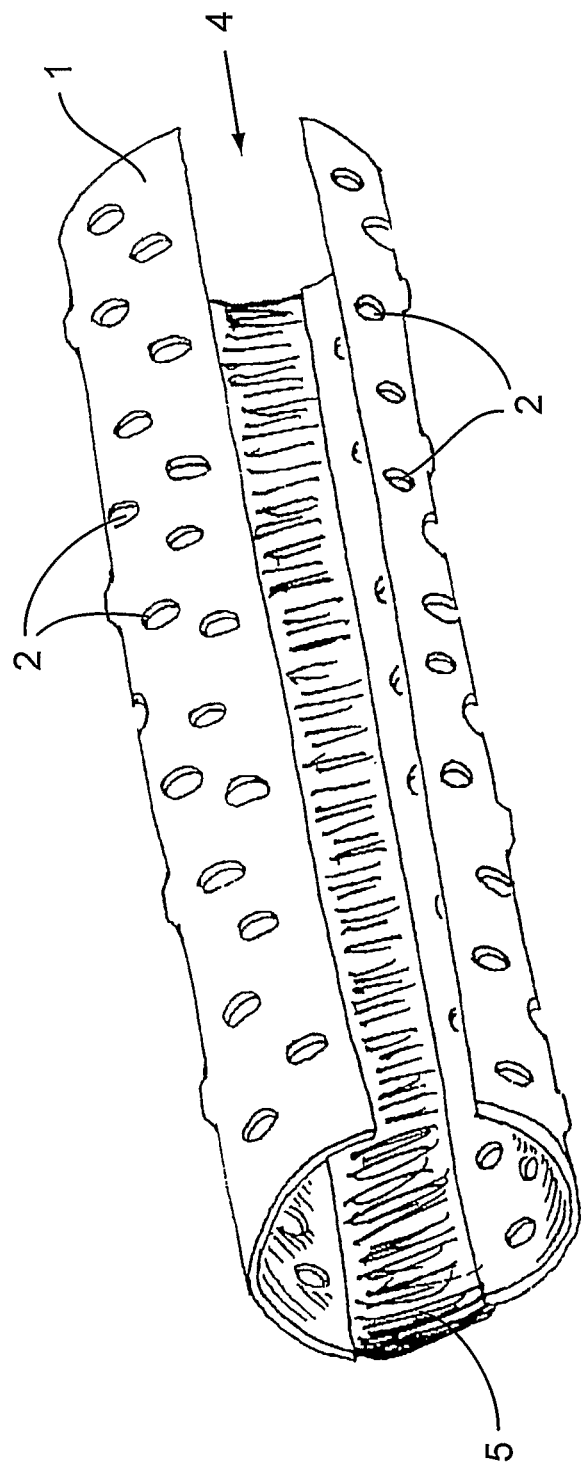
FIG. 3 is a schematic view of a second embodiments of the prosthesis

Self-curative process based on the use of a resorbable polymer inducing fibrotic tissue is known since BIORING SA has patented her annuloplasty prosthesis for use in remodelling a diseased annulus of a natural heart valve described in the document EP 1.284.688.

In the case of present invention, the approach has to be different as far as it shall allow fluid circulation inside the prosthesis but prevent its occlusion by internal cells development. Again, material engineering cannot be directly derived from annuloplasty prosthesis as far as the resulting mechanical and chemical characteristics are to be different as a consequence of applied forces and nature of contact medium (presence of urine leads to accelerated kinetics for resorption process).

The basic idea is the construction of the device in accordance with the invention is to implant, after the cutting through the stricture, a stent from biocompatible resorbable material, which would during temporary time depending on the construction and composition of stent guarantee the complete healing with sufficient size of urethra and prevented the stricture due to the scaring by a fibrous tissue.

Particularly the controllable capacity of resorption of used material is the key to the special construction which on one side permits the drainage of natural secretion of a healthy mucous membrane and on the other side by its character prevents ejection of the stent by urine flow.

Bio-absorbable (or resorbable) materials known to be useful in healthcare industry are either obtained from tissues or proteins coming from animal sources (e.g. collagen or catgut) or yielded by synthetic polymers.

The main polymers known to be bio-absorbable include polyesters, polyorthoesters, polyanhydrides, poly(ether)esters, polyaminoacids and polydepsipeptides.

In other words, bio-absorbable polymers often, but not only, bear the general pattern:

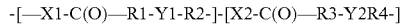

where:
C(O) is a >C=O group,
X1; X2 are an oxygen atom or a NH group,
Y1 (resp. Y2) is an oxygen atom or a NH group or a chemical bond between R1 and R3 (resp. R2 and R4),
R1; R2; R3; R4 are linear or branched, saturated or not, bearing heteroatoms or not, carbon skeletons with (0 or 1) to 10 carbon atoms.

When this general formula is such as X1 is equal to X2; Y1 is equal to Y2; R1 is equal to R3 and R2 is equal to R4, the yielded polymer is called homopolymer. If not, the polymer is called copolymer.

Among these polymers, it has been rapidly preferred polymers with the general formula:

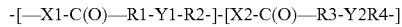

where:
C(O) is a >C=O group,
X1; X2 are an oxygen atom,
Y1 (resp. Y2) is an oxygen atom or a chemical bond between R1 and R3 (resp. R2 and R4),
R1; R2; R3; R4 are linear or branched carbon skeletons with (0 or 1) to 3 carbon atoms.

These polymers include polyglycolydes, polydioxanones, polylactones, polylactides, and polyalkylenecarbonates. To these homopolymers can be added those obtained by copolymerisation of starting monomers.

These polymers are convenient because they are in vivo absorbed according to known processes.

Among these polymers, polydioxanones, and more precisely poly-1,4-dioxanones, were selected because of the absorption kinetics. They are known to be bio-absorbed slower than polylactides or polyglycolides or even than collagen or catgut.

Besides, if the properties of the poly-1,4-dioxanone are suitably adjusted, the material can have softness and rigidity parameters convenient for the application.

Moreover, polydioxanones are today widely used in surgery. Proofs of polydioxanone bio-compatibility and innocuousness have already been widely evidenced.

Again the chosen resorbable material can be dyed be a bio-compatible pigment to improve visibility and even coated (in a bio-reversible manner) by various compounds like siliconized solution, diamond- or pyrolytic carbon or echogenic (contrast) solution or antiseptic solution.

The construction of the device is schematically depicted on FIG. 1.

The device of the present invention can be represented as a tube 1 characterized by dimensional parameters:
D: large inner diameter (in mm)
d: small inner diameter (in mm)
L: device length (in mm)
e: wall thickness (in mm)

By combination of preceding parameters, one can determine de respective values for "Y" (large outer diameter) and "y" (small outer diameter) considering:

$$Y=D+2e$$

$$y=d+2e$$

Together parameters (d,Y,y) leads to an additional characteristic parameter defined as "cone angle". This parameter is named "A" is given by following equation:

$$A=arctg[(Y-y)/L]$$

If values of "Y" and "y" are equal, the device of the invention is then cylindrical (or tubular).

If values of "Y" and "y" are different, the device of the invention is then cylindro-conic, having tubular frusto-conical shape.

The wall thickness "e", as previously defined, can be constant over the all device length or can vary between extremes "$e_{min}$" and "$e_{Max}$". In order to reduce pressure induced by urine flow while maintaining a desired rigidity for the device it can be found convenient to set different values for "$e_{min}$" and "$e_{Max}$" with a positioning of "$e_{min}$" at both extremities of the device and more preferably at the upstream extremity.

FIG. 2 provides with a detail view of the surface of the device. The surface is characterized by the presence of orifices 2 permitting drainage of mucous membrane.

They are characterized by their internal diameter "z" and their density "n" as a number of orifices by surface units (i.e. 100 mm$^2$).

Those orifices have slightly elevated margins 3 for atraumatic immobilization of the device.

The dimension of this margin is characterized by the height "h" with respect to the mean external surface of the device. A too large value for parameter "h" would possibly injure urethral wall cells, a too small value for this parameter would be inefficient. For those reasons "h" will preferably take its values within the range:

$$(y/20) \leq h \leq (Y/5)$$

Under the control of previously introduced parameters, the preferred sets for base parameters (a base parameter is a parameter that cannot be deduce from another base parameter by any of provided equation) are given below:

| | |
|---|---|
| $5.0 \leq Y \leq 50.0$ | mm |
| $y \leq Y$ | |
| $(Y - y) \leq 2.0$ | mm |
| $A \leq 6°$ | angle |
| $5 \leq (L/Y) \leq 15$ | |
| $5 \leq (y/e_{Max}) \leq 20$ | |
| $0.01 \leq z \leq 2.0$ | mm |
| $1 \leq n \leq 20$ | |

In the course of experimental investigation of a suchlike designed urethral device, it has been noticed that a longitudinal split 4 realized on a wall of the device can improve its performance. This split increases the transversal elasticity of the device and the contra-lateral structure 5 is also reinforced by the presence of the split.

FIG. 3 shows a second embodiment of the device with a split.

The invention claimed is:

1. A Device made in a resorbable material intended to be placed in urethra for treatment of stricture,
wherein the resorbable material has the shape of a tube (1), wherein

| | |
|---|---|
| $5.0 \leq Y \leq 50.0$ | mm |
| $y \leq Y$ | |
| $(Y - y) \leq 2.0$ | mm |
| $A \leq 6°$ | angle |
| $5 \leq (L/Y) \leq 15$ | |
| $5 \leq (y/e_{Max}) \leq 20$ | |
| $0.01 \leq z \leq 2.0$ | mm |
| $1 \leq n \leq 20$ | | where $Y=D+2e$; $y=d+2e$, A the angle of the conus and D the large inner diameter, d the small inner diameter, L the length and e the wall thickness of the device in milimeters; z is the internal diameter of the perforations in mm. of the tube and n the number of orifices per 100 mm².

2. The device according to claim 1 wherein the resorbable tube (1) is cylindro-conic or frusto-conical.

3. The device according to claim 1, wherein the resorbable tube (1) is cylindrical.

4. The device according to claim 1, wherein the wall of the tube (1) is perforated by orifices (2).

5. The device according to claim 4, wherein the orifices have margins (3) slightly arisen externally.

6. The device according to claim 1, wherein the tubular wall thickness (e) is constant excepted at one end where it the tubular wall is sharpened.

7. The device according to claim 1, wherein the resorbable material is a homopolymers or copolymers with the sequence
-[—X1-C(O)—R1-Y1-R2-]-[X2-C(O)—R3-Y2-R4-]-
where: C(O) is a >C=O group, X1; X2 are an oxygen atom or a NH group, Y1 (resp. Y2) is an oxygen atom or a NH group or a chemical bond between R1 and R3 (resp. R2 and R4), R1; R2; R3; R4 are linear or branched, saturated or not, bearing heteroatoms or not, carbon skeletons with (0 or 1) to 10 carbon atoms.

8. The device according to claim 7, wherein the resorbable material is polydioxanone.

9. The device according to claim 7, wherein the resorbable material is dyed by biocompatible pigment.

10. The device according to claim 7, wherein the resorbable material is coated by a siliconized solution.

11. The device according to claim 7, wherein the resorbable material is coated by an antiseptic solution.

12. The device according to claim 7, wherein the resorbable material is coated by a contrast (echogenic) solution.

13. The device according to claim 7, wherein the resorbable material is coated by diamond- or pyrolytic carbon.

14. The device according to claim 1, wherein the resorbable material is collagen of bovine, marine or any other biological origin.

15. The device according to claim 8, wherein the resorbable material is dyed by biocompatible pigment.

16. The device according to claim 8, wherein the resorbable material is coated by a siliconized solution.

17. The device according to claim 7, wherein the resorbable material is coated by an antiseptic solution.

18. The device according to claim 8, wherein the resorbable material is coated by a contrast (echogenic) solution.

19. The device according to claim 8, wherein the resorbable material is coated by diamond- or pyrolytic carbon.

* * * * *

UNITED STATES PATENT AND TRADEMARK OFFICE
CERTIFICATE OF CORRECTION

PATENT NO. : 8,486,154 B2  Page 1 of 1
APPLICATION NO. : 12/513405
DATED : July 16, 2013
INVENTOR(S) : Andrieu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1048 days.

Signed and Sealed this
Eighth Day of September, 2015

Michelle K. Lee
*Director of the United States Patent and Trademark Office*